US00PP35318P2

(12) United States Plant Patent
Slaughter et al.

(10) Patent No.: US PP35,318 P2
(45) Date of Patent: Aug. 15, 2023

(54) PEACH TREE NAMED 'WAPEACHFOUR'

(50) Latin Name: *Prunus persica*
Varietal Denomination: Wapeachfour

(71) Applicant: Wawona Packing Co., LLC, Cutler, CA (US)

(72) Inventors: John Keith Slaughter, Fresno, CA (US); Kaylan M. Roberts, Fresno, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 17/803,821

(22) Filed: Dec. 9, 2022

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./197
CPC ... A01H 5/08; A01H 5/00; A01H 6/74; A01H 6/7463
See application file for complete search history.

(56) References Cited

U.S. PATENT DOCUMENTS

| | | | | |
|---|---|---|---|---|
| PP12,019 | P2 * | 7/2001 | Sherman | A01H 5/08 Plt./197 |
| PP14,627 | P3 * | 3/2004 | Byrne | A01H 5/08 Plt./197 |
| PP22,780 | P3 * | 6/2012 | Slaughter | A01H 5/08 Plt./197 |
| PP23,689 | P2 * | 6/2013 | Gerdts | A01H 5/08 Plt./197 |
| PP32,191 | P2 * | 9/2020 | Zaiger | A01H 5/08 Plt./197 |

* cited by examiner

*Primary Examiner* — June Hwu
(74) *Attorney, Agent, or Firm* — Potter Anderson & Corroon LLP

(57) ABSTRACT

A new and distinct variety of peach tree (*Prunus persica*), which is denominated varietally as 'Wapeachfour', and which produces an attractively colored yellow-fleshed, clingstone peach which is mature for harvesting and shipment approximately May 1 to May 10 under the ecological conditions prevailing in the San Joaquin Valley of central California.

1 Drawing Sheet

Botanical designation: *Prunus persica.*
Varietal denomination: 'Wapeachfour'.

BACKGROUND OF THE NEW VARIETY

The present variety of peach tree resulted from an ongoing program of fruit tree breeding. The purpose of this program is to improve the commercial quality of deciduous fruit varieties and rootstocks by creating and releasing promising selections of *Prunus* species. To this end, both controlled and hybrid cross pollinations are made each year to produce seedling populations from which improved progenies are evaluated and selected.

The seedling 'Wapeachfour' was originated by the breeders and selected from a population of seedlings growing experimental orchards located near Fowler, Calif. The seedlings, grown on their own roots, were derived from planting seed of a peach variety 'Burpeachtwentythree' (U.S. Plant Pat. No. 22,780). This maternal parent, which provided the seed of the current variety, was not a controlled cross but was the result from an open pollination or just as likely self-pollination. The resulting fruit was collected from the female parent at a mature stage, and seeds were extracted in August of 2011. The seeds from this tree were embryo-cultured in vitro and subsequently grown in a greenhouse to an appropriate stage before being field-planted and grown into a fruiting stage for evaluation. One yellow-fleshed peach seedling, which is the present variety, exhibited especially desirable characteristics and was designated as 'V2.105'. This seedling was marked for subsequent observation. After the 2015 fruiting season, the new variety of peach tree was selected for advanced evaluation and repropagation.

ASEXUAL REPRODUCTION

Asexual reproduction of this new and distinct variety of peach tree was accomplished by budding the new peach tree onto 30 trees of 'Nemaguard' Rootstock (un-patented). This was performed at an experimental orchard located near Fowler, Calif. Subsequent evaluations of these asexually reproduced plants have shown that the asexual reproductions run true to the original tree. All characteristics of the original tree and its fruit were established and appear to be transmitted through these succeeding asexual propagations.

SUMMARY OF VARIETY

'Wapeachfour' is a new and distinct variety of peach tree. which is considered of relatively large size, and which has a vigorous growth characteristic. This new tree is also a regular and productive bearer of relatively large, firm, yellow-fleshed, clingstone fruit which have a good flavor and eating qualities.

This new peach tree has a medium chilling requirement of approximately 650 hours, and further produces relatively uniformly sized fruit throughout the tree's canopy. In addition to the foregoing, the fruit of the new peach also appears to have good handling and shipping qualities. The 'Wapeachfour' peach tree bears fruit which are typically ripe for commercial harvesting and shipment on approximately May 1 to May 7 under the ecological conditions prevailing in the San Joaquin Valley of central California. In relative comparison to the 'Burpeachtwentythree' peach tree (U.S. Plant Pat. No. 22,780), which is the closest known variety, the current variety of peach tree bears fruit that is both firmer and more uniform than the parent variety. When compared to the seed parent, which is also the presumed pollen parent. the current variety ripens approximately 5 days earlier.

BRIEF DESCRIPTION OF THE DRAWING

FIG. 1 is a color photograph of two whole mature fruit harvested from a sixth leaf year tree displaying both the apical and basal fruit aspects.

One mature fruit is bisected transversely through the equatorial plane revealing the flesh color. In addition, fruit samples display basal, apical, and sutural aspects of the current variety. The external coloration of the fruit as shown in the photograph is sufficiently matured for harvesting and shipment. The colors in this photograph is as nearly true as is reasonably possible in a color representation of this type. Due to chemical development, processing and printing, the fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112 and does not constitute a commercial warranty (either expressed or implied) that the present variety will in the future display all the botanical, pomological, or other characteristics as set forth hereinafter. Therefore, this disclosure may not be relied upon to support any future legal claims including. but not limited to, breach of warranty of merchantability or fitness for any purpose, or non-infringement which is directed, in whole, or in part, to the present variety.

DETAILED DESCRIPTION

Referring more specifically to the pomological details of this new and distinct variety of peach tree, the following has been observed during the fifth fruiting season and under the ecological conditions prevailing at orchards located near the town of Fowler, county of Fresno, state of California. All major color code designations are by reference to The RHS Colour Chart (Royal Horticultural Society, Fourth Edition, 2001) provided by The Royal Horticultural Society of Great Britain. Common color names are also occasionally used.

TREE

Size: Generally considered medium to medium-large in its growth pattern as compared to other common commercial peach cultivars ripening in the early season of maturity. The tree of the present variety was pruned to a height of about 270.0 cm to about 310.0 cm at commercial maturity.

Width: About 260.0 cm.

Vigor: Considered moderate in vigor. The present peach tree variety grew from about 175.0 cm to about 180.0 cm in height during the first growing season. The new variety was pruned to a height of about 150.0 cm after the first dormant season, and primary scaffolds were then selected for the desired tree structure.

Productivity: Productive. Fruit set varies from more than the desired crop load, to levels higher than desired amounts when the new variety is grown in a suitable horticultural zone and under appropriate commercial nursery conditions. The fruit set is spaced by thinning to develop the remaining fruit into the desired market-sized fruit. The number of the fruit set varies with the prevailing climatic conditions and the cultural practices employed.

Fruit bearing: Regular. Fruit set has been adequate during the previous years of observation, and thinning was necessary during the past 5 years on both the original seedling and on subsequent asexually reproduced trees.

Tree form: Upright and pruned into a vase shape.

Density: Considered moderate.

Hardiness: The present tree was grown and evaluated in USDA Hardiness Zone 9. The calculated winter chilling requirements of the new tree is approximately 650 hours at a temperature below 7.0 degrees C.

The present variety appears to be hardy under typical central San Joaquin Valley climatic conditions.

TRUNK

Diameter: About 18.0 cm in diameter when measured at about 15.5 cm above the soil level. This measurement was taken at the beginning of the sixth growing season.

Bark texture: Considered moderately rough with an abundance of lenticles.

Lenticels: Numerous flat, oval lenticels are present. The lenticels range in size from about 3.0 mm to about 5.0 mm in width, and between about 1.0 mm and about 2.0 mm in height.

Lenticel color: Considered an orange brown (RHS Greyed-Orange Group 168 B).

Bark coloration: Variable, but it is generally considered to be a greyed tan (RHS Brown Group 200 B). This bark description was taken from trees in their sixth leaf.

BRANCHES

Size: Considered medium for the variety.

Diameter: Average as compared to other peach varieties. The branches have a diameter of about 11.5 cm when measured during the fifth year after grafting.

Flowering shoot thickness: Average for the species. Generally, the most consistent flower bud development and, therefore, potential fruiting sites occur on shoots which are about 5.0 mm in diameter or larger, but generally less than about 13.0 mm in diameter at the time of bloom.

Surface texture: Average and appearing relatively smooth.

Crotch angles: Primary branches are considered variable and are usually growing at an angle of about 45 degrees when measured from a horizontal plane.

Current season shoots: Surface texture—Substantially glabrous.

Internode length: About 2.0 cm to about 3.0 cm.

Color of mature branches: Approximately Grey brown (RHS Greyed-Orange Group 177 B).

Current season's shoots: Color.—Light green (RHS Yellow-Green Group 145 A). The color of new shoot tips is considered a light green (RHS Yellow-Green Group 144 D).

LEAVES

Size: Considered smaller than average for the species. Leaf measurements have been taken from vigorous, upright, current-season growth, at approximately mid-shoot.
Leaf length: About 145.0 mm to about 155.0 mm.
Leaf width: About 28.0 mm to about 34.0 mm.
Leaf base-shape: The leaves generally exhibit equal marginal symmetry relative to the leaf longitudinal axis.
Leaf form: Lanceolate.
Leaf tip form: Acuminate.
Leaf color:
*Upper leaf surface.*—Medium green (approximately RHS Green Group 137 B).
Leaf texture:
*Upper leaf surface.*—Glabrous.
*Lower leaf surface.*—Glabrous.
Leaf color:
*Lower leaf surface.*—Medium green (approximately RHS Green Group 137 B).
Leaf venation: Pinnately veined.
Mid-vein: Color—Considered a pale green (approximately RHS Yellow-Green Group 145 8). The is no observed different in color on the leaf surfaces.
Leaf margins: Gently undulating.
*Form.*—Considered crenulate.
*Uniformity.*—Generally uniform.
Leaf petioles:
*Form.*—Considered canaliculated.
*Size.*—Considered medium for the species.
*Length.*—About 9.0 mm to about 12.5 mm.
*Diameter.*—About 1.5 mm to about 2.0 mm.
*Color.*—A light green (approximately RHS Yellow-Green Group 145 A).
*Texture.*—Glabrous.
*Strength.*—Durable for species until senescence.
Leaf glands:
*Size.*—Considered relatively small for the species: about 1.0 mm in width; and about 1.5 mm in height.
*Number.*—Generally one per marginal side. Occasionally, two glands per side are found. Observations of more than two glands per marginal side are very uncommon.
*Type.*—Glands located at the base of the leaf are predominantly reniform in shape. An additional one to two, or occasionally more glands. which appear reniform, and stalked, gland primordia are often present at the basal margin of the leaf petiole as well.
*Color.*—Considered a yellowed green (approximately RHS Yellow-Green Group 147 C). Typically, the coloration of the glands darkens and occasionally begins to desiccate relatively early in the growing season.
Leaf stipules:
*Size.*—Medium for this variety.
*Number.*—Typically, 2 per leaf bud and up to 6 per shoot tip.
*Form.*—Lanceolate in form and having a serrated marginal edge.
*Color.*—Green (approximately RHS Yellow-Green Group 144 A).
*Average length.*—about 7.0 mm to about 13.0 mm.

FLOWER BUDS

Hardiness: No winter injury (bud death) has been noted during the last several years of observation in the central San Joaquin Valley. The new variety of peach tree has not been intentionally subjected to drought, cold or heat stress, and therefore this information is not available.
Flower bud: Size—Variable and dependent on the state of maturity. The flower buds as described were observed approximately 7 days prior to bloom.
*Length.*—About 11.0 mm.
*Diameter.*—About 8.0 mm.
*Surface Texture.*—Pubescent.
*Orientation.*—Considered appressed but appear less so as the blossoms near opening.
Bud scale color: Approximately RHS Greyed-Purple Group N186 C.

FLOWERS

Date of first bloom: Observed on Feb. 5, 2022.
*Blooming time.*—Considered average to early bloom in relative comparison to other commercial peach cultivars grown in the central San Joaquin Valley. The date of full bloom was observed on Feb. 12, 2022. The date of full bloom varies slightly with climatic conditions and prevailing cultural practices.
*Duration of bloom.*—Approximately 8 or more days. This characteristic varies slightly with the prevailing climatic conditions.
Flower class: Considered a perfect flower, complete and perigynous.
Flower type: The variety is considered to have a showy-type flower.
Flower size: Considered large. The flower diameter at full bloom is about 44.0 mm to about 50.0 mm.
Bloom quantity: Considered abundant.
Flower bud density: Considered moderately dense.
Flower bud frequency: Generally, two flower buds appear per node. Occasionally, one flower bud per node is observed. Very rarely, three floral buds per node are observed.
Petal size: Generally considered large for the species.
*Petal length.*—About 20.0 mm to about 22.0 mm.
*Petal width.*—About 17.0 mm to 19.0 mm.
Petal form: Considered broadly ovate.
Petal count: Nearly always 5.
Petal texture:
*Upper petal texture.*—Very finely pubescent, satin like.
*Lower petal texture.*—Very finely pubescent, satin like.
Petal color: Considered a light pink at the popcorn stage (RHS Red-Purple Group 62 C).
Fragrance: Slight.
Petal claw:
*Form.*—The claw is considered ovate and is generally medium small.
*Length.*—About 12.0 mm.
*Width.*—About 7.5 mm.
Petal margins: Generally, slightly undulate.
Petal apex: Generally, exhibits a small notch at he apex.

Flower pedicel:
- *Length.*—Considered medium with an approximate length of about 4.0 mm to about 5.0 mm.
- *Diameter.*—About 2.0 mm.
- *Color.*—A medium brown (approximately RHS Grey-Brown Group N199 D) depending on pedicel and fruit maturity and timing of visual observance.
- *Strength.*—Tenacious. Average for the species.
- *Texture.*—Generally smooth.

Floral nectaries:
- *Color.*—Considered a burnt orange (approximately RHS Greyed-Orange Group 163 A).

Calyx:
- *Surface texture.*—Generally glabrous.
- *Color.*—Approximately RHS Greyed-Purple Group 184 B.

Sepals:
- *Upper surface texture.*—Moderately pubescent.
- *lower surface texture.*—Finely pubescent.
- *Number.*—5 sepals.
- *Size.*—Considered medium.
- *Sepal length.*—About 5.0 mm to about 6.0 mm.
- *Sepal width.*—About 4.5 mm to about 6.0 mm.
- *Sepal shape.*—Generally obovate.
- *Sepal margin.*—Considered smooth and entire.
- *Sepal color.*—Approximately RHS Greyed-Purple Group 182 B.

Anthers:
- *Generally.*—Average in size.
- *Color.*—Yellow when viewed dorsally and just prior to dehiscence (approximately RHS Yellow Group 92 C).
- *Position relative to stigma.*—Generally, the stigma is superior to the anthers by about 1.0 mm.

Pollen production: Pollen is abundant and has a yellow color (approximately RHS Yellow-Orange Group 17 D).

Fertility: Self-fertile.

Filaments:
- *Size.*—About 12.0 mm to about 15.0 mm in length.
- *Color.*—Considered white to a pinkish-white (RHS White Group N155 D)

Pistil:
- *Number.*—Usually one, and only rarely more than one.
- *Generally.*—Considered medium in size.
- *Length.*—About 18.0 mm to about 20.0 mm in length including the ovary.
- *Color.*—Considered a very pale pink (approximately RHS Red Group 55 D).
- *Surface texture.*—The variety has a long pubescent pistil.
- *Position relative to petals.*—At flower maturity the stamens grow to be about 1.0 mm to about 1.5 mm superior to the petals.
- *Ovary.*—Pubescent.

FRUIT

Maturity when described: Firm ripe condition (shipping ripe).

Date of first picking: Approximately May 1, 2022.

Date of last picking: May 10, 2022.

Size: Generally—Considered medium-large for the early season of maturity.

Average cheek diameter: About 75.0 mm to about 82.0 mm.

Average axial diameter: About 76.0 mm to about 83.0 mm.

Typical weight: About 215.0 grams. The fruit size and weight can vary and are dependent on the prevailing cultural practices and growing conditions and, therefore, is not particularly distinctive of the new variety.

Fruit soluble solids: About 10.5 to about 12.6 Brix.

Fruit firmness: Fruit flesh pressures generally averaged 12.0 pounds at the time the fruit was analyzed.

Titratable acidity: About 0.82 to about 0.90 at commercial harvest maturity.

Fruit form: Generally—Considered globose. The fruit is generally very uniform in symmetry.

Mucron tip: Can occasionally be observed.

Fruit suture: No stitching exists along the suture line.

Suture: Color—Generally, the fruit appears blushed to the same degree as the skin (approximately RHS Red Group 45 B).

Ventral surface: Form—Considered even, and uniform in appearance, when it is viewed from the lateral, sutural plane.

Apex: Shape—Generally rounded with occasional mucron tip.

Base: Shape—Generally smooth.

Stem cavity: Generally—It extends in a rounded circular form, which is generally considered uniform. The stem cavity is rounded but slightly extended toward the suture. The average depth of the stem cavity is about 9.0 mm to about 11.0 mm. The average width of the stem cavity is about 24,0 mm. The average length of the stem cavity, when measured in the sutural plane, is about 44.0 mm.

Fruit skin:
- *Thickness.*—Considered medium in thickness and tenacious to the flesh.
- *Surface texture.*—Pubescent.
- *Taste.*—Non-astringent.
- *Tendency to crack.*—Not observed in the previous years of observation and evaluation.
- *Density of pubescence.*—medium.

Fruit skin color:
- *Blush color.*—Generally speaking, a red blush exists on much of the skin of the fruit (approximately RHS Red Group 45 B) and is more typically present on the portions of the fruit facing the sunlight. The blush of the fruit typically covers about 80% to about 90% of the fruit skin surface. The fruit blush pattern is considered solid flush.

Ground color: A medium yellow (approximately RHS Yellow-Orange Group 22 B).

Fruit glossiness: Fruit is not considered to be glossy.

Fruit stem:
- *Size.*—Medium in length — about 5.5 mm to about 7.5 mm.
- *Diameter.*—About 2.0 mm o about 3.0 mm.
- *Color.*—Pale yellow green (approximately RHS Yellow-Green Group N144 D).

Fruit flesh:
- *Ripening.*—Considered even.
- *Texture.*—Firm, juicy, and dense. Considered non-melting in flesh classification.
- *Fibers.*—Present, but not prominent.
- *Aroma.*—Present.
- *Eating quality.*—Considered good.
- *Flavor.*—Considered balanced with sweetness and acidity.
- *Juice production.*—Moderate.
- *Brix.*—About 10.5 degree to about 12.6 degrees.

*Acidity.*—Considered medium. Approximately 0.84 titratable acidity at fruit harvest. Acid levels assayed from fruit flesh can vary with fruit maturity, length of time in cold storage, sunlight exposure, and climatic, regional, seasonal, and cultural influences.

*Flesh color.*—It is considered yellow (approximately RHS Yellow-Orange Group 14 C).

Anthocyanin colorization: Unremarkable anthocyanin coloration throughout the flesh of the fruit. and from stone to skin.

STONE

Type: Considered a clingstone.

Size: It is generally considered to be medium for the species.

Length: Average, about 28.0 mm to about 32.0 mm.

Width: Average, about 21.0 mm to about 25.0 mm.

Diameter: Average, about 14.0 mm to about 17.5 mm.

Form: Roughly ovoid.

Stone base: Shape—The stone is considered shortly attenuate.

Apex: Shape—The stone exhibits a slight acute tip.

Stone surface:

*Surface texture.*—Peach varieties that ripen this early generally exhibit poorly and somewhat undefined stones, which is also true of the present variety. The stones have not yet lignified at time of fruit maturity and are considered to be soft and papery in texture. Considered irregularly furrowed toward the apex. Further, more pitting exists in the mid-portion of the stone (laterally) and is more common toward the base.

*Ridges.*—Ridging is generally more prominent and is usually oriented parallel and laterally relative at the ventral and dorsal margins. Stone pitting is observed nearer the apex while smaller pitting is found nearer to the base.

*Ventral edge.*—The ventral edge is generally described as having adjoining ridges formed from each hemisphere. There are longitudinal grooves running alongside this joined ventral suture.

*Dorsal edge.*—Shape — Generally considered moderately rough. The folds of the surface ridges appearing somewhat irregular on the external margins, creating an uneven face.

Stone color: The color of a mature, dry stone is generally considered a pale yellow (approximately RHS Yellow Group 14 C).

Tendency to split: Splitting has rarely been noted.

Kernel:

*Length.*—About 15.0 mm to about 17.0 mm.

*Width.*—About 10.0 mm to about 12.0 mm.

*Thickness.*—About 4.0 mm to about 5.5 mm.

*Size.*—The kernel is considered medium in size.

*Form.*—Considered generally ovoid. The kernel shape is often irregular and of a pasty texture as the cotyledons are neither formed nor firm.

*Kernel surface texture.*—Kernel pellicle is shortly pubescent.

*Color.*—A pale yellow (RHS Yellow-Orange Group 19 D).

Use: The present variety 'Wapeachfour' is a peach tree of the early season of maturity and which produces fruit which are considered to be firm, attractively colored, and which are useful for both local and long-distance shipping.

Keeping quality: Appears excellent. The fruit of the present variety has stored well for periods of up to 21 days after harvest at 1.0 degree Celsius.

Shipping quality: Good. The fruit of the new peach tree variety showed minimal bruising of the flesh or skin damage after being subjected to normal harvesting and packing procedures.

Time of beginning of leaf bud burst: Approximately January 20.

Resistance to insects and disease: No susceptibilities were noted. The present variety has not been intentionally tested to expose or detect any susceptibilities or resistances to any known plant or fruit diseases, insects, frost, winter injury, or other environmental factors.

Although the new variety of peach tree possesses the described characteristics when grown under the ecological conditions prevailing near Fowler, Calif., in the Central part of the San Joaquin Valley of California, variations of the usual magnitude and characteristics incident to changes in growing conditions, fertilization, nutrition, pruning, pest control, frost, climatic variables, and changes in horticultural management are to be expected.

Having thus described and illustrated our new variety of peach tree, what we claim is new, and desire to secure by Plant Letters Patent is:

1. A new distinct variety of peach tree named 'Wapeachfour' substantially as illustrated and described, and which is characterized principally as to novelty by producing an attractively colored yellow-fleshed, clingstone peach which is mature for harvesting and shipment approximately May 1 to May 10 under the ecological conditions prevailing in the San Joaquin Valley of central California.

* * * * *

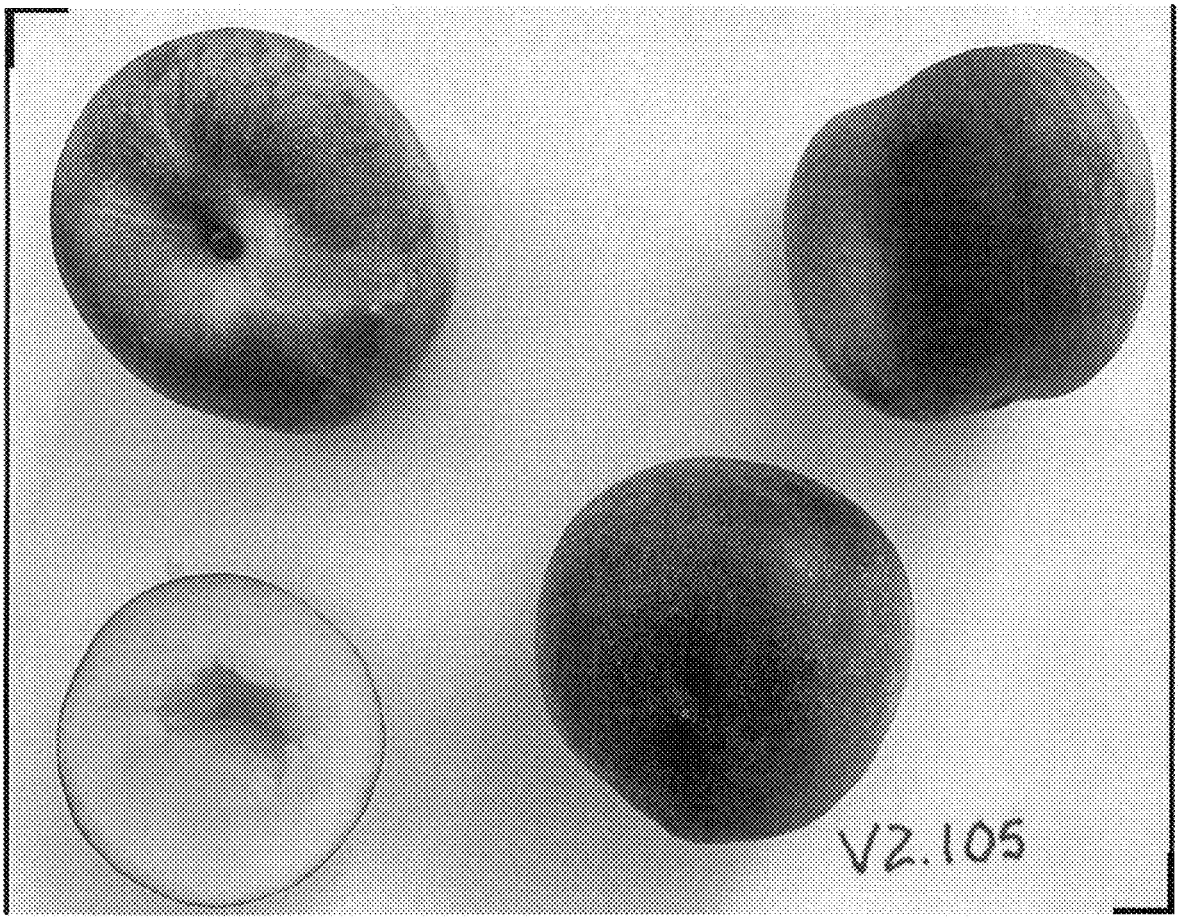
V2.105